United States Patent [19]
Dam

[11] Patent Number: 5,733,574
[45] Date of Patent: Mar. 31, 1998

[54] NICOTINE CONTAINING STIMULANT UNIT

[76] Inventor: Anders Dam, Sollerod Park 16-St. 3, DK-2840 Holte, Denmark

[21] Appl. No.: 481,843

[22] Filed: Jun. 7, 1995

Related U.S. Application Data

[63] Continuation of Ser. No. 170,455, Dec. 20, 1993, Pat. No. 5,424,049, which is a continuation of Ser. No. 859,516, Jun. 8, 1992, abandoned.

[30] Foreign Application Priority Data

| Nov. 7, 1989 | [DK] | Denmark | 5560/89 |
| Dec. 4, 1989 | [DK] | Denmark | 6156/89 |
| Nov. 6, 1990 | [WO] | WIPO | PCT/DK90/00280 |

[51] Int. Cl.[6] .................. A61K 9/22; A61K 9/24; A61K 9/50
[52] U.S. Cl. .............. 424/464; 424/48; 424/468; 424/469; 424/478; 424/488; 424/479; 424/434; 424/435
[58] Field of Search .................. 424/48, 464, 440, 424/468, 469, 478, 488, 479, 447, 435, 434; 426/3; 514/813

[56] References Cited

U.S. PATENT DOCUMENTS

| 369,365 | 12/1887 | Dudley . | |
| 2,122,982 | 7/1938 | Leo . | |
| 2,600,700 | 6/1952 | Smith . | |
| 3,293,045 | 12/1966 | Griffin . | |
| 3,368,567 | 2/1968 | Speer . | |
| 3,429,308 | 2/1969 | Russell | 128/1 |
| 3,555,144 | 1/1971 | Pazar et al. . | |
| 3,870,794 | 3/1975 | Hutchinson et al. . | |
| 4,039,653 | 8/1977 | DeFoney et al. | 424/19 |
| 4,059,686 | 11/1977 | Tanaka et al. | 424/19 |
| 4,374,082 | 2/1983 | Hochschild . | |
| 4,572,832 | 2/1986 | Kigasawa et al. | 424/19 |
| 4,755,386 | 7/1988 | Hsiao et al. | 424/435 |
| 4,764,378 | 8/1988 | Keith et al. | 424/435 |
| 4,774,093 | 9/1988 | Provonchee et al. . | |
| 4,915,948 | 4/1990 | Gallopo et al. | 424/435 |
| 4,940,587 | 7/1990 | Jenkins et al. | 424/480 |
| 5,135,753 | 8/1992 | Baker et al. . | |
| 5,147,648 | 9/1992 | Bannert . | |
| 5,158,772 | 10/1992 | Davis . | |
| 5,196,202 | 3/1993 | Konishi . | |
| 5,549,906 | 8/1996 | Santus | 424/440 |
| 5,593,684 | 1/1997 | Baker et al. | 424/435 |

FOREIGN PATENT DOCUMENTS

| 0 135 264 | 6/1984 | European Pat. Off. . |
| 0251642 | 1/1988 | European Pat. Off. . |
| 0252306 | 1/1988 | European Pat. Off. . |
| 58-128314 | 7/1983 | Japan . |
| 60-142927 | 7/1985 | Japan . |
| 61-122211 | 6/1986 | Japan . |
| 62-142113 | 6/1987 | Japan . |
| 1 388 786 | 4/1972 | United Kingdom . |
| 2142822 | 1/1985 | United Kingdom . |

OTHER PUBLICATIONS

Delcaration of Henning Gjelstrup Kristensen Appendix A—Curriculum Vitae—Henning Gjelstrup Kristensen.
European Pharamacopaeia, Second Edition, Part II, 1992.
USP XXII; NF XVII; The United States Pharamacopeia, The National Formulary, 1990.
Marintdale, The Extra Pharmacopoeia; 26th Edition, Norman W. Blaco, ed., p. 739.
Remington's Pharmaceutical Sciences, 18th Edition, Mack Publishing Company, p. 1664.

*Primary Examiner*—Thurman K. Page
*Assistant Examiner*—Sharon Howard
*Attorney, Agent, or Firm*—Merchant, Gould, Smith, Edell, Welter & Schmidt, P.A.

[57] ABSTRACT

The present invention relates to a saliva-soluble stimulant unit comprising an active ingredient in a gel, wherein the gel is prepared by gelling a water-binding gelling agent, and the active ingredient comprises nicotine or alkaloid having the same direction of activity, said unit having a texture profile, with parameter values of firmness, hardness, brittleness, adhesiveness, elasticity and cohesiveness within given ranges; a disintegration time within the range 5–60 minutes; and a nicotine content from 0.5 to 10 mg.

25 Claims, 1 Drawing Sheet

NICOTINE CONTAINING STIMULANT UNIT

This is a continuation of application Ser. No. 08/170,455, filed Dec. 20, 1993, now U.S. Pat. No. 5,424,049 which is a continuation of application Ser. No. 07/859,516 filed Jun. 8, 1992, now abandoned which applications are incorporated herein by reference.

1. BACKGROUND OF THE INVENTION

1. Field of the Invention

The present invention relates to a saliva-soluble nicotine containing stimulant unit.

It is a generally recognized fact that active as well as passive smoking of tobacco products such as pipe tobacco, cigars and cigarettes presents serious hazards to public health as well as to the social environment.

It is an equally recognized fact that giving up a smoking habit presents serious problems for a person accustomed to smoking tobacco.

These problems are mainly due to nicotine addiction. It has actually been established that addicted smokers experience an urgent need for tobacco stimulation when the nicotine concentration in the person's blood plasma drops to about 15 ng/ml.

It is further known that various nicotine-containing smokeless stimulants may be used alleviating this urge and thereby assisting smokers to give up their smoking habits without noticable inconvenience.

2. Prior Art Disclosure

Smokeless nicotine stimulants in form of smokeless tobacco products such as chewing tobacco and snuff have been known for a long time, and various improvements have been suggested.

U.S. Pat. No. 1,376,586 discloses a product comprising fine cut or chewing tobacco in the form of tablets or individual "chews" and having surfaces entirely covered by chicle gum that is impervious to both air and moisture and effective in preventing the evaporation of the tobacco juices.

U.S. Pat. No. 4,545,392 discloses a smokeless tobacco product comprising cut or otherwise comminuted tobacco and 1–35 weight-% of a non-saccharide water-insoluble masticable gum base composition, calculated on the basis of dry tobacco weight, optionally including water-soluble gums such as gum arabic for stabilizing the gum composition, and formulated in the form of pieces of cut or otherwise comminuted tobacco having said masticable gum base composition adhered to the surface as a discontinous coating. According to the citation the individual particles of tobacco should hereby tend to remain dispersed in the mouth.

PCT Patent Application No. WO 81/02090 discloses a chewing tobacco product in the form of individual portions in which chewing tobacco is coated widen or distributed as small particles in a solid or semisolid carrier material. As carrier material, chewing gum is preferred. However, it is further mentioned that starch hydrolysates, e.g. non-sticky products used in the production of "gum drops", may be used as carrier material, although such use is not illustrated by way of examples. Further, the carrier material may contain additives such as flavours, sweeteners, and dried water-soluble extracts of natural product such as coffee or tee extracts.

Nicotine containing sprays or aerosols for oral use are known e.g. from DE-OS 32 41 437 and GB-PS 15 28 391. Nicotine administration by means of a spray or an aerosol does, however, only provide a short term effect.

A nicotine containing preparation for nasal use is known from DE-OS 34 01 763. However, nasal use is rather unpleasant, since the nose mucous is more sensitive than the mouth mucous. Furthermore this administration too provides only a short term effect. Nasal administration must therefore also be considered less appropriate.

DE-OS 34 38 284 discloses a deposit plaster giving off nicotine by which, however, only a very slow and rather uncontrolled absorption of nicotine is obtained. Further the desirable sudden increase of the nicotine concentration in users' blood plasma and the accompanying physiological experience corresponding to that of the first puffs by smoking a cigarette cannot be achieved by use of a deposit plaster.

A chewable smoking substitute composition in the form of a nicotine containing chewing gum is disclosed in U.S. Pat. No. 3,901,248. This composition comprises about 15 to about 80 percent gum base and a nicotine cation, exchange resin complex dispersed in the base. The cation exchange resin complex constitutes up to about 10% of the chewing gum composition and affords a nicotine release, when chewed, of approximately that available when smoking a conventional cigarette.

Other improved chewable smoking substitute compositions which are relatively non-irritating to the throat are disclosed in U.S. Pat. No. 3,845,217. These improved compositions comprise about 15 to 80 weight percent gum base, nicotine, and at least one solid physiologically acceptable water soluble buffering agent capable upon chewing of maintaining the pH of the saliva above the normal physiological pH of the saliva, i.e. about 7.4.

The nicotine may be present in a form selected from the group consisting of nicotine free base, a water soluble physiologically acceptable salt thereof, nicotine sorbed on a physiologically acceptable adsorbent, and nicotine in the form of a complex with an insoluble cation-exchanger.

The amount of nicotine present calculated as the free base is from 1 to 10, preferably from about 1 to about 3 mg per chewing gum unit.

In order to obtain a controlled, not too rapid release of nicotine it is preferred to incorporate nicotine as a complex with an insoluble cation-exchanger.

Other chewable smoking substitute compositions of the chewing gum type are disclosed in FR patent application, publ. number 2 608 156. These compositions contain nicotine incorporated in particles which are provided with a surface layer of a water soluble material which allegedly should lead to a controlled, not too rapid release of nicotine.

Generally, smokeless tobacco products based on cut tobacco and carrier materials, e.g. chewing tobacco, communited tobacco distributed in water-soluble gum bases (chewing gums), or starch hydrolysates (gum drops), according to the prior art provide residues of tobacco and/or carriers which are insoluble or difficult to dissolve in the saliva.

Besides that the disposal of these residues may be unpleasant and socially unacceptable, the amounts of ingredients from cut tobacco at the levels required to obtain a nicotine stimulation are high and cause pain in the stomach.

An undesirable sudden release of ingredients e.g. nicotine and flavours may occur by using smokeless tobacco products having a brittle or crystalline type texture when these products are crunched. Hereby large fresh areas of the product may be exposed and the user may receive a large concentrations of the ingredients and consequently experience undesirable variations in the expected physiological effects of the stimulation.

Similar uncontrolled releases of nicotine can occur with nicotine-containing chewing gums when kneaded during mastication.

BRIEF DESCRIPTION OF THE DRAWING

The sole FIG. 1 describes the relationship of force(N) to deformation.

2. DISCLOSURE OF THE INVENTION

The saliva-soluble stimulant unit

Figure 1:
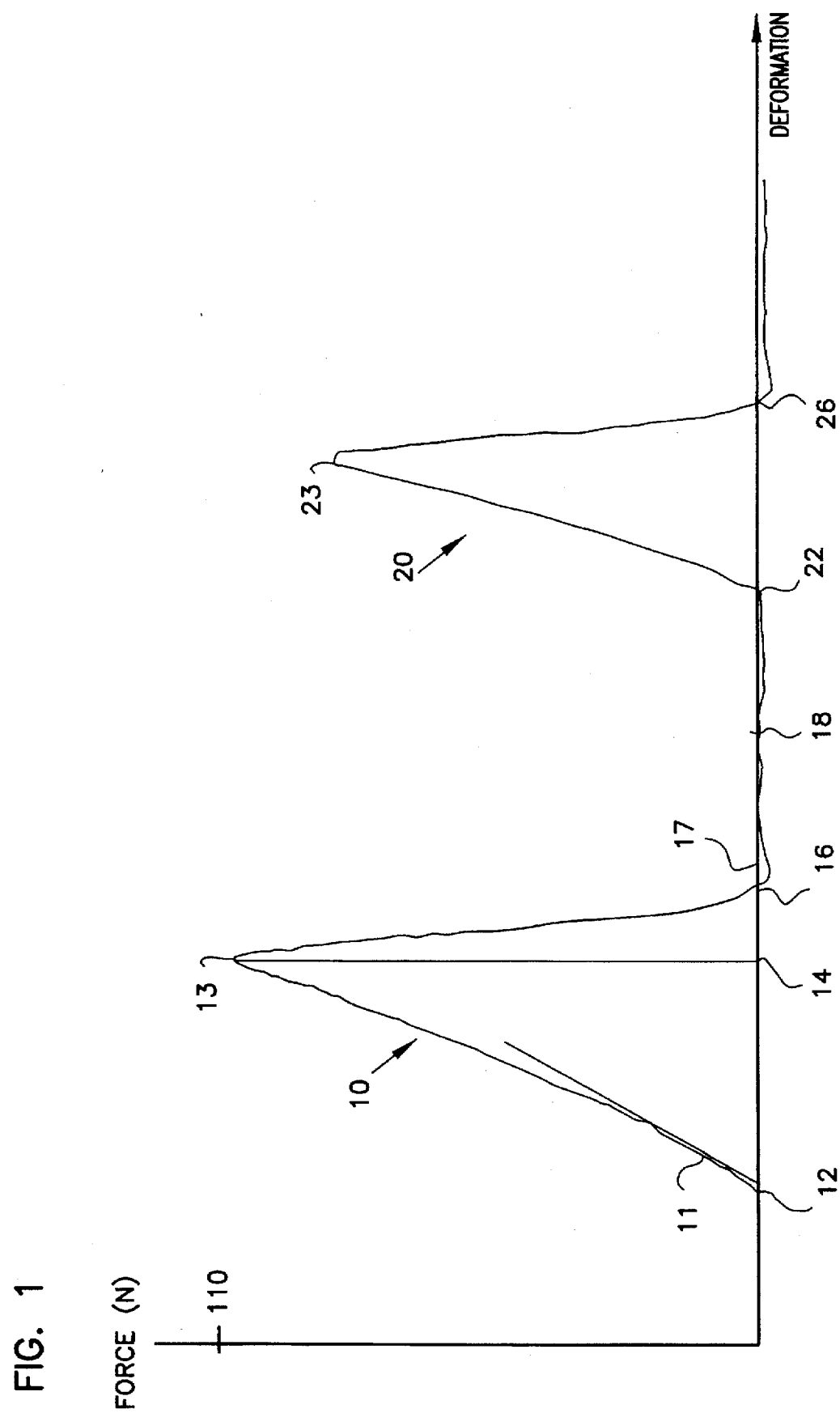

It is the primary object of the present invention to provide a tobacco supplement or tobacco substitute product in the form of a nicotine-containing stimulant unit for oral use which provides a controlled release of nicotine and optionally additional ingredients, e.g. flavouring and aromatizing additives.

Specifically it is the object of the invention to provide a nicotine-containing saliva-soluble stimulant unit providing a nicotine stimulation which is improved in relation to or at least similar to the stimulation obtained by known products of smoke tobacco such as cigarettes, cigars, pipe tobacco, and the tobacco substitute products mentioned above; simultaneously avoiding residues of tobacco, and/or carrier; undesirable variations in physiological effects; and unpleasant disposal of known tobacco and tobacco substitute products.

It is also the object of the invention to provide a saliva-soluble stimulant unit allowing oral use under various conditions including simultaneous intake of beverages, such coffee, wine or beer; and formulated to provide a nicotine dose corresponding to the stimulation of nicotine obtained by smoking a cigar, a fill of pipe tobacco, or preferentially a cigarette.

According to the invention a controlled release of nicotine and a release of optional ingredients such as flavour and aroma additives from a smokeless nicotine stimulation can be obtained by a salive-soluble stimulant unit comprising a gel prepared by gelling a water-binding gelling agent; nicotine or other alkaloids with same direction of activity; and optional ingredients such as flavour and aroma additives; and having a well-defined texture profile, as defined below, comprising a set of mechanical properties, viz. firmness, hardness, brittleness, adhesiveness, elasticity, and cohesiveness; and having a selected concentration of nicotine or said alkaloids.

Accordingly, in its broadest aspect, the invention provides a saliva-soluble stimulant unit comprising an active ingredient, and optional ingredients comprising flavour and aroma additives incorporated in a gel prepared by gelling a water-binding gelling agent, in which the active ingredient comprises nicotine or other alkaloids with the same direction of activity, said unit having i) a texture profile, determined by texture profile analysis, with parametre values within the following ranges:
  a) firmness, i.e. modulus, greater than 100 N/cm$^2$;
  b) hardness, i.e. maximum force occuring during a first cycle compression, greater than 5 N/cm$^2$;
  c) brittleness, i.e. strain percentage required to break the gel, of at least 30%;
  d) adhesiveness, i.e. the ratio between the area of the negative peak between two compression cycles and the area of the first peak, from 0 to 70%;
  e) elasiticity, i.e. the ratio 100×(D–d)/D, where D is the sample height (cm) before the first compression cycle, and d is the permanent deformation of the sample (cm) before the second compression cycle, within the range from 25 to 100%;
  f) cohesiveness, i.e. total work ratio between the first and second compression cycle, within the range from 25 to 100%;

ii) a disintegration time, measured at 37° C. using a disintegration test apparatus according to Ph.Eur. second edition, within the range 5–60 minutes; and iii) a nicotine content from 0.5 to 10 mg or a corresponding content of said alkaloids.

The disintegration time is measured at 37° C. using a disintegration test apparatus according to Ph.Eur., second edition, V. 5.1.1., under conditions further described below. It should be observed that the physiologically observed disintegration time by other use has a value which is about one third of the disintegration time as defined above.

The terms "texture profile" and "texture profile analysis" are defined and described in G. Sanderson et al., "Gums and Stabilisers for the Food Industry 4", Proceedings of the 4th International Conference, Wrexham, Clwyd, Wales, July 1987, IRL Press, Ltd. (1988), and Szczesniak, et al., J. Food Science 28 (1963) 385–403, which are incorporated by reference.

By the variant of the texture profile analysis used in the present context, a force-deformation curve is obtained by successively compressing a sample twice to 70% of its original height using a selected compression rate. Objectively measurable physical parameter values closely related to the sensory textural characteristics of firmness, hardness, brittleness, adhesiveness, cohesiveness and elasticity are derived from the force-deformation curve.

Thus,
a. firmness is measured by the initial slope (modulus) of the force-deformation curve expressed in force per unit area;
b. hardness is measured by the maximum force per unit area that occurs at any time during the first cycle compression;
c. brittleness is measured by the first significant drop of the force-deformation curve during the first compression cycle, i.e. the point of first fracture, expressed as the % deformation required to break the sample;
d. adhesiveness is measured (in the present context) as the ratio between the area of the negative peak between two compression cycles and the area of the first peak;
e. elasticity is measured as the ratio 100×(D–d)/D, where D is the sample height (cm) before the first compressin cycle, and d is the permanent deformation of the sample (cm) before the second compression cycle; and
f. cohesiveness is measured by the ratio between the peak-areas of the second and first compression cycle expressed in %.

It has been found that by choice of a texture according to the invention controlled release of nicotine is ensured because the exposed surface area of the stimulant unit is kept essentially constant during eating, i.e. during the succesive dissolution of surface layers of the stimulant unit;

because significant deformation of the stimulant unit is avoided during mastication; and because the ingredients contained in a given volume element of the stimulant unit is only released when that volume element is exposed to the surface and the volume element matrix is dissolved by the saliva.

The selected ranges of:

hardness and brittleness ensure that the exposed surface area is not suddenly increased by fracturing of the stimulant;

firmness, elasticity and cohesiveness ensure that the stimulant cannot be kneaded during mastication; and adhesiveness ensures that the stimulant unit does not stick, e.g. pulls fillings out of the teeth.

Preferred and particularly preferred texture profile parameter values and disintegration times appear from claims 2 and 3.

Buffer substance or agent

Absorption of nicotine from the saliva to the blood plasma is dependent on pH of the saliva, pH of the plasma, and the pKa (=8.02) of nicotine.

Assuming a pH of the plasma of 7.4 and of the saliva of 7.0 only about 30% of the nicotine will be in the free base form. Thus, in order to promote absorption of nicotine, the pH of the saliva must be increased. At pH 8.5 about 80% of the nicotine is in the free base form and about 3.8 times the total plasma concentration of nicotine is about 3.8 times the total saliva concentration based on the formula $$[1+10^{-(pHp-pKa)}]/[1+10^{-(pHp-pKa)}]$$

described by Martin et al., Clin. Pharmacol. Ther. 16, 1052–1058, (1974).

Thus, according to a preferred embodiment, a stimulant unit comprises additives of physiologically acceptable buffering substances or agents and amounts thereof selected to ensure a pH of the saliva of 8–10 during disintegration of the unit. Particularly, the amount of buffering substances or agent in a sitmulant unit is from 5 to 50 mg per unit.

Nicotine doses

The stimulant units are formulated to provide a nicotine dose corresponding to the stimulation of nicotine obtained by smoking e.g. a cigarette.

Thus, in a preferred embodiment, the amount of nicotine in the stimulant unit is adjusted to provide a nicotine dose in the range from 0.5 to 5.0 mg nicotine per unit. The amount of nicotine in a stimulant unit can be chosen to provide a given nicotine stimulation which is sensed as e.g. light, medium, or strong. Particularly preferred ranges are from 1.0 to 1.5 mg of nicotine, from 1.5 to 2.5 mg of nicotine, and from 2.5 to 3.0 mg of nicotine per unit.

Release profiles of nicotine

The stimulant units are formulated to provide desired nicotine release profiles.

"Continous release"

Thus, according to a preferred embodiment, continous release of nicotine, i.e. a prolonged essentially constant release, is provided by a homogeneous distribution of nicotine throughout the stimulant unit.

Generally, the nicotine release profile depends on the effective surface area of the unit during disintegration. Thus, to a first approximation ignoring edge effects, the unit disintegrates with a constant rate of release of nicotine which gradually declines as the unit diminishes.

"Priming and sustained release"

Further, according to another preferred embodiment, a two-step release comprising a priming and a sustained release of nicotine is provided by an inhomogeneous distribution of nicotine in a multi-layered stimulant unit with i) an outer layer formulated to have a short disintegration time and a suitable amount of nicotine to provide a priming release which can bring the nicotine concentration in the blood plasma of the user above the lowest effective concentration in the blod plasma; and ii) an inner layer formulated to provide longer disintegration times and suitable amounts of nicotine to provide a sustained release keeping the plasma concentration of nicotine above the lowest effective concentration for the desired length of time.

Shapes of stimulant units

The nicotine released from nicotine-containing stimulant units according to the invention is predominantly absorbed orally in the oral cavity when the unit is placed either under the tongue (sublingually), against the cheek (buccally), or against the palate (palatally). Thus, the nicotine-containing stimulant unit may be of any shape suitable for adherence at these locations.

Further, when shaped suitably, the sitmulant unit is fixed and can be eaten during simultaneous intake of beverage.

In a preferred embodiment, the stimulant unit is shaped such that it fits wholly or partly the shape of the palate.

Procedure of use

Nicotine-contaning stimulant units according to the invention may be used to obtain a nicotine stimulation similar to that obtained from smoking or non-smoking tobacco products by oral intake of a suitably chosen stimulant unit, placing the unit against the desired location in the oral cavity by means of the tongue, and gently sucking or licking the unit at a pace chosen for an individual sensory perception and stimulationary effect of nicotine.

3. DETAILED DESCRIPTION (a) Texture profile analysis

Within the present context, the term "texture of material" is used to designate a characteristic consistency of the material. The texture of a material can be described objectively as a set of values for six physical parameters, the "texture profile" measured by the texture profile analysis described by Sanderson et al. as mentioned above.

In the following the calculation of the values of these parameters, i.e. of the texture profile, is explained referring to the drawing which shows a force-deformation curve (at 20° C.), of a cylindrical test sample of a stimulant unit having a diameter of 15,4 mm and a height of 12,3 mm comprising two successive compression cycles to 70% of the original height of the sample using a compression rate of 50 mm/minute.

The texture profile comprises a first compression cycle 10 and a second compression cycle 20. From the first compression cycle 10, a firmness (modulus) of 169 N/cm$^2$ is measured as the initial slope 11 of the curve at the origin 12 of the beginning of deformation times the height of the sample before compression, and divided by the sample end surface area.

Further, a hardness of 58 N/cm$^2$ is measured as the maximum force 13 (height of the first peak) occurring at any time during the first compression cycle 10, i.e. at the strain level 14, divided by the sample end surface area.

A brittleness of more than 30% is measured as the point of first fracture (which was not reached in this test), i.e. the brittleness is larger than 30% for the present sample, since the sample was compressed to a 30% strain level 14 without fracture (a large number indicates a non-brittle texture).

An adhesiveness of about 4% is measured as the ratio of the negative peak area 17 following the first compression cycle 10 to the peak area of the first compression cycle. If the material is adhesive, it will adhere to the compression plates and pull the plates in the opposite direction of their movement between the two compression cycles.

An elasticity of 85% is measured by the ratio between the height D (12.3 mm) of the sample before the first compression cycle 10 minus the deformation d (1.8 mm), i.e. the distance 22–18, to the height D of the sample before the first compression cycle. The origin 18 of the second compression cycle, is found as twice the 30% deformation distance 14–12.

A cohesiveness of 57% is measured as the ratio between the peak-areas of the second and first compression cycles. To a first approximation this peak-ratio can be estimated by the ratio between the peak heights, i.e. 23 and 13, times the ratio between the base lines of the peaks, i.e. the distances 26–22 and 16–12. Alternatively, the peak areas can be calculated numerically by computer, or graphically by a planometer, or by weighing replicates of the peak areas.

(b) Active ingredient

According to the invention the active ingredient can be selected from the group consisting of:
- nicotine (3-(1-methyl-2-pyrrolidinyl)-pyridine) including synthetic nicotine and nicotine extracts from tobacco plants, such as the genus Nicotiana; and
- other alkaloids with the same direction of activity including nor-nicotine and lobeline, e.g. of the species Lobeliaceae and Lobelia; methylanabasine and anabasine;
- alone or in combination; and
- in the form of free base or pharmacologically acceptable acid addition salts.

Further, the active ingredient can include various oxidation products such as nicotine-1'-N-oxide.

(c) Water-binding gelling agent

An important factor for obtaining the desired texture of the stimulant unit according to the invention is the choice of a suitable water-binding gelling agent.

According to the invention the water-binding gelling agent can be selected from the group consisting of:
- organic gelling agents including gelatine, modified and unmodified starch; and
- gums including agar, alginate, arabic gum, carob gum, carrageenan, ghatti gum, guar gum, karaya gum, pectin, tragacanth gum, locust beam gum, and xanthan gum.

Preferred gelling agents comprises gum arabic, starch, gelatine, agar, and pectin. Particularly for hard gums, gum arabic alone constituting about 50–70% of the total solid matter is preferred. However, for softer stimulant compositions, another gelling agent, e.g. gelatine, is required such as gelatine, just as more than one water-binding gelling agent can be used simultaneously.

(d) Optional ingredients

Optional ingredients comprises additives for sweetening, flavouring, aromatizing, coloring, and stabilizing, as well as vitamines and minerals and buffering substances or agents to provide a pH of saliva which promotes nicotine transfer to the blood plasma.

"Sweeteners"

Sweetners may comprise one or more synthetic or natural sugars, i.e. any form of carbohydrates suitable for use as sweetener in the manufacture of confectionary products.

According to the invention sweeteners can be selected from the group consisting of:
- single sugars including sugars extracted from sugar cane and sugar beet (sucrose), dextroxe (also called glucose), fructose (also called laevulose), and lactose (also called milk sugar); sorbitol, mannitol, glycerol, xylitol, sodium saccharin; and
- mixtures of sugars including glucose syrup, e.g. starch hydrolysates, containing a mixture of dextrose, maltose and a range of complex sugars, invert sugar syrup, e.g. sucrose inverted by invertase (also called sucrase or sacchrase) containing a mixture of dextrose and fructose, high sugar content syrups such as treacle and honey containing a mixture of particular leavulose, dextrose, maltose, sucrose, ressins, dextrin and higher sugars; and malt extracts.

"Flavour and aroma additives"

The flavour and aroma additives can comprise one or more synthetic or natural flavouring or aromatizing agents.

According to the invention flavour and aroma agents can be selected from
- essential oils including distillations, solvent extractions, or cold expressions of chopped flowers, leaves, peel or pulped whole fruit comprising mixtures of alcohols, esters, aldehydes and lactones;
- essences including either diluted solutions of essential oils, or mixtures of synthetic chemicals blended to match the natural flavour of the fruit, e.g. strawbery, raspberry and black currant; artificial and natural flavours of brews and liquors, e.g. cognac, whiskey, rom, gin, sherry, port, and wine; tobacco, coffee, tea, cocao, and mint;
- fruit juices including expelled juice from washed, scrubbed fruits such as lemon, orange, and lime; liquorice, menthol, eucalyptus, aniseeds nuts (e.g. peanuts, coconuts, hazelnuts, chestnuts, walnuts, colanuts), almonds, raisins; and
- powder, flour, or communited vegetable material parts including tobacco plant parts, e.g. genus Nicotiana, in amounts not contributing significantly to the level of nicotine, and ginger.

Particularly preferred natural flavour and aroma agents are selected from essential oils, essences, powder, flour, or communited plant parts of tobacco plants in amounts not contributing significantly to the level of nicotine.

Particularly preferred additional flavour and aroma agents are selected from the group consisting of essential oils and essences of tobacco, coffee, tea, cocao, and mint.

"Colouring additives"

According to the invention colouring additives can be selected from dyes containing chemical grouping which absorb light including dyes resistant to the presence of reducing sugars and confectionary acids; dyes resistant to heat and light, dyes that do not separate into basic colours; particular useful dyes are mixtures of tartrazine and indigo carmine producing a pea green colour; mixtures of erythrosine and indigo carmine producing purple; and mixtures tartrazine, amarath and indigo carmine producing chocolate brown; caramel containing burnt sugar for brown coloring either as powder or liquid; carbon black producing black; and titaniumdioxide producing white.

"Stabilizing additives"

According to the invention stabilizing additives can be selected from the group consisting of
- antioxidants including vitamin E, ascorbic acid, sodium pyrosulfite, buthylhydroxytoluene, and buthylhydroxytoluene; and
- preservatives including citric acid, tartaric acid, lactic acid, malic acid, acetic acid, benzoic acid, and sorbic acid.

"Vitamins and minerals"

It has been shown that smokers because of smoking may lose vitamins and minerals, particularly C-vitamins. This loss can be compensated by stimulant compositions containing vitamin and mineral additives.

Therefore, according to the invention, optional ingredients may comprise one or more vitamins and mineral additives.

Preferred vitamins are selected from the group consisting of A, B1, B2, B6, C, D2, D3, E, F, K, and P-vitamins, particularly C-vitamins.

Preferred minerals are selected from a group consisting of magnesium, iron, zinc, cobber, iodine, manganese, chromium, selenium, molybdenum, cobalt, vanadium, nickel, tin, fluorine and silicon.

However, in adding vitamine and mineral additives to compositions according to the invention care should be taken not to break down the vitamines, e.g. breaking down the vitamines A, B, C, and E by contact with air, and practically all vitamines by high temperatures. Further, vitamines and minerals may have inherent strong flavours, which are difficult to mask, just as they may adversely effect other ingredients, particularly acids. Also, vitamines may be instable to light and slowly deteriorate during storage.

"Buffering substances or agents"

According to the invention buffering substances or agents can be selected from the group consisting of physiologically acceptable buffering substances or agents which can stabilize a pH value in the range from about 6.5–9, including alkali metal carbonate and bicarbonate or phosphate systems particularly sodium carbonate and sodium bicarbonate; potassium carbonate and potassium bicarbonate; trisodium phasphate, disodium hydrogen phosphate, and sodium dihydrogen phosphate; and tripotassium phosphate, dipotassium hydrogenphosphate, and potassium dihydrogenphosphate; and mixtures thereof.

(e) Preparation of stimulant units

Important parameters determining the texture of the stimulant unit comprise recipe, pH value and temperature of the starting mixture or solution and the process conditions in the subsequent process steps where the starting mixture/solution is transferred/dewatered to "green units" which are subsequently cured/dewatered to stimulant units. When products, such as gums, jellies and pastilles are produced by dewatering in starch or rubber moulds care should be taken to ensure that the final moisture content has a suitable value which usually is less than 20%, depending mainly on the chosen gelling agent.

Stimulant units according to the invention can be produced by a number of methods known in the art, see "Sugar Confectionary and Chocolate Manufacture", R. Lees and E. B. Jackson, Leonard Hill Books (1973), which is incorporated by reference, including methods of producing gum arabic gum, agar gellies, gelatine jellies, starch gum jellies and pastilles; starch jellies such as orange slices, jujubes, and jelly beans; fruit pastilles such as wine gums, gum-based pastilles, tablet jellies, tablets, lozenges, liquorice paste, and pectin jellies.

Specific recipes and methods for manufacture of gelled water-binding agents (known art)

(a) Gum arabic gum

| RECIPE | |
| --- | --- |
| | Parts by weight |
| Gum Arabic | 100 |
| Cold Water | 120 |
| Sugar | 90 |
| Glucose Syrup | 14 |
| Water | 15 |
| Colour, Flavour and Acid to desired shade and taste | |

Method of preparation

1. Slowly dissolve the gum arabic pieces in water.
2. Carefully sieve the solution through a fine sieve or cloth, to remove impurities and extraneous material.
3. Dissolve the sugar in the water, add the glucose syrup and boil to 124° C. (256° F.).
4. Add the boiled solution to the gum arabic solution and mix well.
5. Mix and allow to stand for at least one hour. (During this standing time, the mixture will begin to clear and foam will rise to the surface. This crust should be removed before continuing.)
6. Add the colour, flavour and acid solution.
7. Mix.
8. Deposit into starch moulds.
9. Transfer the moulded impressions to a drying stove and hold until the desired hardness is achieved.
10. Thoroughly clean the gum jellies and glaze.

(b) Agar jellies

| RECIPE | |
| --- | --- |
| | Parts by weight |
| Agar | 2.0 |
| Water | 70.0 |
| Sodium Citrate | 0.7 |
| Sugar | 60 |
| Glucose Syrup | 40 |
| Colour, Flavour and Acid | to taste |

Method of preparation

1. The agar, depending on source, should be pre-soaked in cold water for 3–12 hours.
2. Slowly heat the mixture in an open steam pan to bring about solution.
3. Add the sodium citrate.
4. Strain through a fine sieve.
5. Add sugar and glucose syrup to the agar solution and boil until a temperature of 107° C. (225° F.) is reached.
6. Cool to a temperature not exceeding 76° C. (170° F.), and add any acid solution.
7. Add the colour and flavour.
8. Deposit in warm dry starch moulds.
9. Hold the jellies in starch moulds for 12–24 hours.
10. Check that the total soluble solids content of the finished jellies is in excess of 76% before removing from starch.

The moulding starch shold be in the range 5–8% moisture and be held at 26°–43° C. (79°–110° F.).

(c) Gelatine Jellies

| RECIPE | |
| --- | --- |
| | Parts by weight |
| Powdered Gelatine 180 Bloom | 25 |
| Hot Water | 50 |
| Sugar | 80 |
| Glucose Syrup | 80 |
| Water | 40 |

Method of production

1. Prepare the gelatine solution in advance, by slowly adding the specified weight of powdered gelatine to warm water. Mix to obtain a solution and allow to clear.
2. Dissolve the sugar in water and add glucose syrup. Boil to a temprature of 116° C. (241° F.).
3. It is advantageous at this stage to cool this solution to approximately 70° C. (158° F.), before adding to the gelatine solution.

4. Add the boiled solution to the gelatine solution and mix in.
5. Add the dissolved colour and acid solution and mix. Add the required flavour and mix in.
6. Deposit into starch moulds.
7. Transfer the moulded impressions to a drying stove and hold until the desired hardness is achieved.

If sheet or granular gelatine is used, it should be pre-soaked for a minimum of three hours in its own weight of water. In most factories it is usual to soak overnight.

(d) Starch Gum Jellies and Pastilles

RECIPE

| Ingredient | A B Gums | Hard | Soft Fruit Pastilles | Medium Hard Pastilles |
|---|---|---|---|---|
| Sugar | 40.0 | 34.0 | 30.0 | 40.0 |
| Glucose Syrup | 40.0 | 54.0 | 48.0 | 48.0 |
| Thin Boiling Starch | 12.5 | 12.0 | 12.0 | 11.0 |
| Water | 100.0 | 120.0 | 110.0 | 100.0 |
| Jam | | | 10.0 | |
| Colour, Flavour, Acid | | As required | | |

General Method of Production

1. Boil the sugar and glucose syrup with two-thirds of the water in a steam-jaketed pan.
2. Prepare a starch slurry using the remaining water.
3. Slowly add the starch slurry to the boiling sugar mixture, the speed of addition being such as not to cause the mixture to cease boiling. Vigourous stirring at this stage will help.
4. Continue cooking until the necessary consistency is reached.
5. Add the colour, flavour, and acid solution.
6. Deposit into starch impressions and stove in a hot room for 24 hours.

The jam can be prepared by boiling 50% sugar with 50% fruit pulp. The types of thin boiling starches which are recommended are acid or oxidised, with a fluidity of 20, 30, 40 and 50.

(e) Starch Jellies (continous production)
RECIPE

BASIC STARCH JELLY

| | Parts by weight |
|---|---|
| Sugar | 25 |
| Glucose Syrup 42 DE | 25 |
| Water | 19 |
| 75 fluidity Thin Boiling Starch | 10 |
| Colour, Flavour and Acid | As required |

Method of preparation

1. Add eater to pre-mixing pan (Cold).
2. Add sugar and mix (Cold)
3. Add starch and mix (Cold)
4. Add glucose syrup and mix.
5. Raise the temperature to 80°–90° C. (176°–194° F.).
6. Check total solids of pre-mix at 20° C. (68° F.) on refractometer. The jelly should be within the range 76–82%.
7. Pump to cooker.
8. Check total solids content after cooking: this should not vary by more than 2% water.
9. Deposit into search impressions and in a hot room for 24 hours.

ORANGE SLICES (Starch Base)

| | Parts by weight |
|---|---|
| Glucose Syrup | 200.0 |
| Dextrose | 104.0 |
| Sugar | 200.0 |
| Starch (85 fluidity) | 60.0 |
| Water | 100.0 |

Total Solids 76%–80%. Cooking Temperature 278°–283° F. Texture: Short/Tender.

JUJUBES

| | Parts by weight |
|---|---|
| Glucose Syrup | 200.0 |
| Sugar | 160.0 |
| Starch (75 fluidity) | 64.0 |
| Dextrose | 80.0 |
| Water | 80.0 |

Total Solids 78%. Cooking Temperature 275°–285° F. Texture: Short/Harder.

JELLY BEANS

| | Parts by weight |
|---|---|
| Water | 132.0 |
| Starch (70 fluidity) | 60.0 |
| Glucose Syrup | 330.0 |
| Sugar | 130.0 |

Total Solids 68%–70%. Cooking Temperature 285°–295° F. Texture: Firm/Chewy.

(f) Fruit Pastilles
RECIPE
A: STARCH-BASED PASTILLES

| | Parts by weight |
|---|---|
| Sugar | 90.0 |
| 36 DE Glucose Syrup | 90.0 |
| Water | 35.0 |
| Thin Boiling Starch (60 fluidity) | 20.0 |
| Gelatine (medium Bloom) | 12.0 |
| Fruit Pulp | 16.0 |
| Tartaric Acid | 3.5 |
| Colour and Flavour to Taste | |

Method of preparation

1. Add sugar to water bring to the boil.
2. Add glucose syrup bring to the boil.
3. Slowly add starch slurried in 50 parts cold water boil 10 mins.
4. Add fruit pulp boil to 110° C. (23° F.).
5. Cool to 93° C. (200° F.).
6. Add gelatine dissolved in 24 parts hot water.
7. Add colour, flavour and acid dissolved in 5.0 parts water.

8. Deposit in warm dry starch.
9. Place in a stove at 54° C. (130° F.) for 48 hours.
10. Clean off starch and coat with crystal sugar or wet crystallise.

B: GUM-BASED PASTILLES

|  | Parts by weight |
| --- | --- |
| Sugar | 100 |
| Glucose Syrup | 75 |
| Water | 30 |
| Prepared Gum Arabic Solution | 100 |
| Gelatine | 10 |
| Water | 20 |
| Colour, Flavour and Acid to taste | |

Method of preparation
1. Dissolve sugar in water, add glucose syrup, boil 127° C. (260° F.).
2. Stir the prepared gum arabic solution.
3. Dissolve gelatine in double its own weight of hot water.
4. Add to batch at 82° C. (180° F.).
5. Add colour, flavour and acid dissolved in an equal weight of water.
6. Deposit in warm dry starch.
7. Stove at 54° C. (130° F.) to required texture.

(g) Tablet Jellies

| RECIPE | |
| --- | --- |
|  | Parts by weight |
| Cane or Beet sugar | 280 |
| Invert Sugar Syrup (70%) | 245 |
| Water | 70 |
| Batch yield | 595 |

Method of preparation
1. Run the required quantity of hot water into a large heated pan.
2. Raise the temperature to 90° C. (194° F.).
3. Add the specified weight of cane or beet sugar and dissolve.
4. Add the specified weight of invert sugar syrup, mix.
5. Run through a filter press.
6. Hold at 60° C. (140° F.) until required.

Boiling
7. Draw off 590 parts of syrup.
8. Rapidly boil until the temperature reaches 123° C. (252° F.). Alternatively pass through a heat exchanger to concentrate the syrup to 90% total soluble solids.

Cooling
9. Turn on the cooling units and bring the syrup temperature down to 100° C. (212° F.).

Preparation of Other Ingredients
Gelatine
10. Slowly add 80 parts of gelatine to 145 parts of hot water at 90° C. (194° F.) in a mixer tank.
11. Operate the mixing blades at low speed until the syrup is discharged into the tank.

Acid
12. Dissolve 12 parts of citric acid in 12 parts water.

Buffer
13. Dissolve 2.5 parts sodium citrate in 2.5 parts of water.

Flavouring and Colouring (as desired)
14. Measure 0.45 parts flavouring and add to the batch.
15. Dissolve 0.025 parts of colouring in 0.25 parts water and add.

Mixing
16. Gravity feed or pump the syrup after the completion of stage 8 into gelatine mix at stage 11.
17. Allow to mix for 3–5 minutes.
18. Up to 5% scrap jelly can be incorporated at this stage.
19. Add the buffer solution, flavouring, colouring and finally the acid.
20. When the mixing is complete stop the paddles and transfer to the pouring hopper passing the jelly liquor through a wide mesh sieve.

Depositing
21. Allow the scum to rise.
22. Ensure that the holding slabs or moulds are well covered with release agent.
23. Deposit at a sufficiently slow raze to avoid the incorporation of air bubbles.

(h) Tablets

| RECIPE | |
| --- | --- |
|  | Parts by weight |
| Icing Sugar | 100 |
| Stearic Acid | 0.75 |
| Isopropanol | 1.25 |
| Gelatine | 0.75 |
| Glucose Syrup | 0.5 |
| Water | 4.0 |
| Flavouring | 0.125 |

Method of preparation: Wet Granulation
1. Dissolve the stearic acid in the isopropanol.
2. Dissolve the gelatine in the requisite amount of warm water and blend in the glucose syrup.
3. Place the icing sugar in the bowl of the mixer.
4. Add the liquid components and work into the batch.
5. Check that the mixture forms a ball when held in the hand.
6. If the mix is of a satisfactory consistency, granulate and pass through a suitable mesh (normally No. 6) to form a small granular mix.
7. Spread the crumbled dough on a tray and transfer to drying ovens.
8. Dry at 60° C. (140° F.) for 10 hours.
9. Transfer to a tumbler mixer and add the lubricant and flavouring. Mix.
10. Transfer to the tableting units and compress to shape.

(i) Lozenges

| RECIPE | |
| --- | --- |
|  | Parts by weight |
| Icing Sugar | 300 |
| Gum Solution A | |
| Gum Arabic | 4 |
| Water | 6 |
| Gelatine Solution | |
| Gelatine (100 Bloom) | 5 |
| Water | 3 |

-continued

| RECIPE | |
|---|---|
| | Parts by weight |
| Gum Solution B | |
| Gum Tragacanth | 0.03 |
| Water | 0.5 |
| Flavouring | 2 |

Method of preparation
1. Place the icing sugar in the mixer.
2. Prepare the gelatine mix with water which is no hotter than 80° C. (176° F.).
3. Add the gum solutions (prepared the previous day) to the gelatine mix. Strain the gum/gelatine solution and mix before use.
4. Blend the flavour into a proportion of the icing sugar and add to the remainder of the batch.
5. Add the gelatine/gum mix to the icing sugar.
6. Mix slowly and thoroughly for such time as is necessary for the particular version of mixer in use.
7. Discharge into containers and transfer to the feed hopper of the stamping unit.

Size: Large lozenges—200/lb (440/kg); Small lozenges—500/lb (1100/kg); Cachons—1000/lb (2200/kg).

Variants
Pan Room Centres
Add 10 parts of cornflour at stage 1—this will produce lozenges which are harder and less likely to break in the revolving pans.

Coloured and Scented Lozenges (Cachons)
Use 0.05 parts of colouring to produce the desired pastel shade and scent with 0.02 parts of violet, peach blossom, rose and lilac perfumes.

(j) Liquorice-Paste

| | RECIPE | | |
|---|---|---|---|
| | "Open Pan" Batch | | "Continuous |
| Ingredient | Sheet Parts by weight | Novelties Parts by weight | Cooking" Sheet Parts by weight |
| Slurry Water | 50 | 50 | — |
| Wheat Flour | 150 | 150 | 125 |
| Mix Water | 130 | 160 | 80 |
| Brown Sugar | 125 | 100 | 60 |
| Crude Treacle | 75 | 150 | 140 |
| Hydrol | 25 | — | 25 |
| Glucose Syrup (high DE grade) | 12.5 | 12.5 | 10 |
| Block Juice | 20 | 25 | 18 |
| Dissolving Water | 15 | 20 | 10 |
| Liquid Caramel | 15 | 25 | 10 |
| Hardened Palm Kernel Oil | 2.5 | 2.5 | 2.5 |
| Aniseed Oil | 0.25 | 0.25 | 0.25 |
| Black Colour | 1 | 1 | 1 |
| Salt | 0.5 | 0.5 | 0.5 |
| Water | 5 | 5 | — |
| Gelatine | 5 | 5 | — |
| GMS | 0.5 | 0.5 | 0.5 |
| Cooking time, minutes | 80 | 150 | |
| Pump speed and temperature should be controlled according to quality required | | | |
| Scrap addition — no more than: | 25 | 50 | 25 |

Red liquorice can be prepared by leaving out the liquid caramel and substituting golden syrup for treacle. Add 1 part of red colour to produce a bright red shade omitting the black colouring.

Method A—Continuous process
1. Place the glucose syrup and water in the jacketed disintegrator/agitator pan and add the brown sugar. Mix.
2. Raise the temperature to 40° C. (104° F.).
3. Break up the block juice and add to 1 gal of hot water; heat to dissolve and add to the premix.
4. Add any remaining ingredients and prepare a homogeneous slurry by recycling for 20 minutes.
5. Raise the temperature to 60° C. (140° F.) and recycle the mix for a further two minutes.
6. Pump into the votator unit at constant speed (machine setting is determined by the desired product texture).

Method B—Batch process
1. Place the slurry water in a stirring pan and add the wheat flour; blend.
2. Run the mix water into the cooking pan, heat to boiling and add the hydrol, brown sugar, salt and the block juice (previously dissolved in boiling water).
3. For liquorice sheet only, add the treacle, glucose syrup and molasses.
4. Continue heating and when boiling run in the starch slurry.
5. When all the starch slurry has been added, bring to the boil and cook for the specified period.
6. For liquorice novelties and plug only, the required weights of treacle glucose syrup and molasses should be added 30 minutes prior to the end of the cooking period.
7. On completion of the cook period, release heat and add the liquid caramel, aniseed flavouring, black colour and the prepared gelatine solution.
8. Mix until a constant shade is achieved.
9. Discharge the cooked mass and transport to the extruders.

Method C—BCH "HK" flowline plant
1. Mix the liquid ingredients of an unmodified "batch" recipe and transfer to the slurry premix unit.
2. Start the pan agitator and add any remaining "solid" raw materials; recycle to prepare a homogeneous premix.
3. Turn on
   (a) the steam in the FM cooker
   (b) the extractor fan to remove any evaporated water, and
   (c) the water flow in condenser unit positioned in the vapour vent.
4. Pump the premix into the cooker and commence cooking.
5. Observe the level of the condensed water collected in the measuring tank and the amperage reading. (Note—the amount of water condensed is indicative of the rise in solids content, while the rise in power consumption will indicate the progression of gelatinisation.)
6. As soon as the amount of condensed water has reached the calculated level to give the desired moisture content of the liquorice paste at the end of cooking turn off the steam, the fan and the cooling water.
7. Discharge the cooked paste on to a conveyor and transport to the extruder. Extrude at 70°–82° C. (158°–180° F.).
8. Pass the extruded sheet through a 40 ft cooling tunnel for 1½–5 minutes (depending on shape) and guillotine or cut to size with rotary cutters.

(k) Pectin Jellies
RECIPE

(A) Buffered Slow Set Pectins

| | Parts by weight |
|---|---|
| Pectin | 1.25 |
| Citric Acid Monohydrate | 0.4 |
| Sugar | 51 |
| Glucose Syrup 42 DE | 29 |
| Water | 40 |
| Colour and flavour | As required |
| Yield | 100 |

(B) Buffered Slow Set Pectins (using 63 DE Glucose Syrup)

| | Parts by weight |
|---|---|
| Pectin | 1.25 |
| Citric Acid Monohydrate | 0.4 |
| Sugar | 38 |
| Glucose Syrup 63 DE | 42 |
| Water | 37 |
| Colour and Flavour | As required |
| Yield | 100 |

Formula (A) produces a moderately firm jelly, whilst formula (B) gives a slightly more tender product.

(C) Unbuffered Slow Set Pectins

| | Parts by weight |
|---|---|
| Pectin | 0.82 |
| Citric Acid Monohydrate | 0.28 |
| Potassium Citrate | 0.25 |
| Sugar | 51 |
| Glucose Syrup | 29 |
| Water | 40 |
| Colour and Flavour | As required |
| Yield | 100 |

The amount of citric acid monohydrate used will depend upon the type of pectin. For some types of unbuffered slow set apple pectins, 0.28 parts would be required, while for unbuffered slow set citrus pectin, 0.4 parts of citric acid should be used.

(D) Unbuffered Slow Set Pectins (using 63 DE Glucose Syrup)

| | Parts by weight |
|---|---|
| Pectin | 0.82 |
| Citric Acid Monohydrate | 0.28 |
| Potassium Citrate | 0.25 |
| Sugar | 38 |
| Glucose Syrup | 42 |
| Water | 37 |
| Colour and Flavour | As required |
| Yield | 100 |

Methods for Continuous Production

For continuous production, it is necessary to first prepare a stable pectin solution. The pectins most suitable are slow set buffered and low methoxyl (buffered). It is essential to ensure complete solution before use. Failure to do so can result in weak gel formation and inefficient utilisation of the full gelling power. It is recommended that Solutions are made up to a known concentration by weight, and advice should be taken from the pectin manufacturer as to the type and solubility of the buffer salt used.

| PECTIN SOLUTION | |
| --- | --- |
| | Parts by weight |
| Pectin | 2 |
| Sugar | 10 |
| Water | 88 |

Method of preparation

1. Mix the pectin and sugar in the dry state.
2. Place water in mixing vessel and heat to 70°–77° C. (158°–170° F.).
3. Start the stirrer and add the pectin-sugar mixture to the water.
4. Heat to boiling point and stir for one minute.
5. Cool the solution to 50°–60° C. (122°–140° F.).

Cooling is necessary to prevent degradation of the pectin. It can be omitted if the solution is to be used immediately.

Other recipes for manufacturing gums, gellies, and pastilles can be found in a series of articles "gum-gellies-pastilles, part 1.-6." by "Sweetmaker" in Confectionary Production, starting from June 1983 to November 1983, which references are incorporated by reference.

In the following the invention is illustrated by a number of examples:

4. EXAMPLES

General considerations:

In the following examples are listed a number of formulations which may be used for the manufacture of stimulant units according to the present invention.

The manufacture of the stimulant unit is based on the preparation of a liquid, homogenous composition comprising sugar, water, the selected saccharides and/or carbohydrate materials as well as, if so desired, raw materials of animal origin such as gelatine. Colouring additives, flavouring additives, preservatives and other additives may be added to this composition, which is kept in such a state regarding temperature and viscosity, that it may be cast to form the desired units. It is recommended that the active ingredient, i.e. nicotine, and eventually the buffer substance or agent, is added to the composition shortly before the process of casting is carried out. This procedure is recommended in order to safeguard accurate control with the highly potent chemical substance, nicotine, whereby the total quantity of active substance used in the manufacture during a specific period of operation must correspond to the content of active ingredient in the finished product plus the content of active ingredient in any added material. Any added material may according to the formulation and procedure used be remelted for use in a subsequent production or if this for any reason is not feasible such material should be carefully collected and destroyed for instance by incineration.

The production of stimulant units according to the present invention may be carried out using any suitable method of production known to a person skilled in the art. Such methods, in particular the preparation of suitable solutions of polysaccharides and/or starches and/or gelatine and subsequent mixing of such solutions with solutions of sugar (including other carbohydrates such as dextrose sirups) are to be selected in accordance with the choice of raw materials, which will lead to end products of suitable texture and showing characteristics within the limit of parametres as outlined above.

The method of manufacture which is normally used consists in casting the liquid composition in suitable cavities produced in a starch material typically by making an impression in such clean, moistore/conditioned starch material of suitable size and shape immediately prior to the casting. Other methods of casting may if so desired be employed such as the use of mold made from flexible materials such elastomers. In special cases stimulant units according to the present invention may also be produced by other known methods such extrusion and subsequent cutting, or by the punching of tablets from suitable mixture of ingredients in the form of powders or granulates.

After solidification during a suitable period of time at controlled temperature and relative humidity in the surrounding air the stimulant units are removed from the starch material by any known method, cleaning any excess starch material from the stimulant units for instance by brushing and/or blowing with a stream of air, and it is recommended to submit the product to a so-called glazing or polishing treatment with an oily material, which may be applied directly or in the form of a solution in a volatile solvent, and which leaves a thin coating giving the finished article an attractive surface-gloss, non-stickiness and resistance to variations of water content either in the shape of drying out or of taking up water from the surrounding atmosphere.

Whilst in the examples the method of manufacture is based on batch production or more or less manually controlled casting in trays containing the starch material, any partially or fully automated method of production, such as the use of the so-called "Mogul" machinery may be used, although conversion to such high-speed production techniques normally will require certain adjustments to be made in the composition of the material ready for casting.

In the examples the following materials were used:

RAW MATERIALS:

Dextrose sirups, Glycosum Liquidum (Lot no. 302 589) Mecobenzon, Denmark;

Sugar (preferably caster sugar), Dansukker Melis, DDS, Denmark;

Gum arabic (cleaned), Gummi Arabicum (chemically pure powder LK (E 414), (lot no. 233 200), Nordisk Droge Handels A/S, Denmark;

Gelatine (preferably bloom 215), Gelatine powder 215 B (lot no. 232 883), Nordisk Droge Handels A/S, Denmark;

Tap water;

Tobacco dust, granulate of Half and half pipe tabacco, American Branch;

Citric acid;

Essence of peppermint;

Anis;

Essence of almond; and

Cocoa.

Materials for Drying

Corn starch, Maydis Amylum (lot no. 257 329), Mecobenzon, Denmark;

Wheat starch, Tritici Amylum (lot no. 257 535), Mecobenzon, Denmark;

The starch material must be dried at 150°–200° C. for at least 2 hours before use to a moisture content not exceeding 10%.

Solutions of gum arabic

Solution 1 (50% gum arabic)

3.5 kg of water heated to 30° C. was slowly poured into 3.5 kg of gum arabic under constant stirring, then vigorously stirred, and left standing for approx. 20 hours. The solution was skimmed off and left standing 1 hour. Before use the solution was skimmed off again.

Solution 2 (50% gum arabic)

3.5 kg of gum arabic was stirred slowly into 3.5 kg of water held at 30° C., and treated as described for solution 1.

Solution 3 ( 33.3% gum arabic)

2 kg of warm water (30° C.) was slowly stirred into 1 kg of gum arabic, and treated as described for solution 1.

Pre-soaked gelatine solutions

Solution 4 (33.3% gelatine)

900 g of gelatine was slowly stirred into water (12° C.), then 900 g of warm water (70° C.) was stirred into the solution, which was left standing for 20 hours.

Note: Solution 4 could not be used without reheating and filtration.

Solution 5 (33.3% gelatine)

900 g of gelatine was slowly stirred into 1800 g of warm water (70° C.), then vigorously stirred, and left standing for 20 hours.

Solution 6 (33.3% gelatine)

1800 g of warm water (50° C.) was slowly stirred into 900 g of gelatine, then vigorous stirred, and left standing for 20 hours.

Solution 7 (33.3% gelatine)

150 g of gelatine plus 300 g of water was placed in a vessel, heated slowly to 95° C., and, when all material was melted, cooled to 50° C. and used immediately.

Solution 8 (25% gelatine)

1800 g of warm water (70° C.) was slowly poured into 600 g of gelatine under stirring, then vigorous stirred, and left standing for 20 hours.

Preparations

Percent dry weight is indicated in parenthesis.

Recipe A 210 g sugar (25%)

210 g dextrose (25%)

50 g water 420 g gum arabic (50%) (1260 g solution no. 3)

Water and sugar was stirred together and heated until the sugar was melted. Dextrose was added and the mixture was slowly heated to 125° C. (boiling time 23 minutes). Gum arabic was added and the mixture was slowly boiled for 80 minutes. Then the mixture was left standing for 3 hours at 35° C. The mixture had a final pH of 4.0–5.0.

The mixture was thoroughly skimmed from the top. Then the mixture was poured into units of corn starch moulds and dried at 50° C. to a moisture content of 5–10%.

Recipe B 210 g sugar (19%)

365 g dextrose (32%)

60 g water 560 g gum arabic (49%) (solution no. 1)

Water and sugar were stirred together and heated until the sugar was melted. Then dextrose was added and the mixture was heated to 125° C. (boiling time 55 minutes). Gum arabic was stirred into the mixture and heated to 75° C. Then the mixture was left standing for 1.5 hours at 35° C. The mixture had a final pH of 5.0–5.5.

The mixture was thoroughly skimmed from the top. Then the mixture was poured into units of corn starch moulds and dried at 50° C. to a moisture content of 5–10%.

Recipe C 210 g sugar (24%)

350 g dextrose (41%)

55 g water 300 g gum arabic (35%) (solution 1)

The mixture of sugar, etc., prepared as described in section A and B was heated to 117° C. (boiling time 20 minutes). Gum arabic was added and heated to low boiling. The mixture was left standing for approx. 1 hour at 35° C. The mixture had a final pH of 4.5–5.5.

The mixture was thoroughly skimmed from the top. Then the mixture was poured into units of corn starch moulds and dried at 50° C. to a moisture content of 5–10%.

Recipe E 210 g sugar (23%)

210 g dextrose (23%)

60 g water 480 g gum arabic (53%) (solution no. 2)

The sugar mixture was boiled for 23 minutes up to 118° C. Gum arabic was stirred into mixture. Then the mixture was left standing for 1.5 hours at 35° C. The mixture had a final pH of 3.5–5.0.

The mixture was thoroughly skimmed from the top. Then the mixture was poured into units of corn starch moulds and dried at 50° C. to a moisture content of 5–10%.

Recipe F 210 g sugar (17%)

360 g dextrose (30%)

60 g water 640 g gum arabic (53%) (solution no. 2)

The sugar mixture was boiled to 122° C. (boiling time 20 minutes), and the mixture was cooled to 115° C. Gum arabic was added. The the mixture was left standing 1.5 hours at 35° C. The mixture had a final pH of 3.0–5.0.

The mixture was thoroughly skimmed from the top. Then the mixture was poured into units of corn starch moulds and dried at 50° C. to a moisture content of 5–10%.

Recipe G 210 g sugar (23%)

280 g dextrose (31%)

70 g water 400 g gum arabic (44%) (solution no. 2)

25 g gelatine (3%) (solution no. 8)

The sugar mixture was boiled to 140° C. (boiling time 25 minutes). Gum arabic was added and the mixture was cooled to 80° C. Then gelatine was heated to 70° C. and added to the mixture. The mixture was left standing for 80 minutes at 35° C. The mixture had a final pH of 4.0–5.0.

The mixture was carefully skimmed from the top. Then the mixture was poured into units of wheat starch moulds and dried at 50° C. to a moisture content of 5–10%.

Recipe H 210 g sugar (33%)

280 g dextrose (44%)

50 g water 150 g gelatine (23%) (solution no. 5)

The sugar mixture was boiled to 120° C. (boiling time 25 minutes). The the mixture was cooled to 90° C. Gelatine was heated to 70° C. and added to the mixture. The mixture was left standing for 35 minutes. The mixture had a final pH of 4.0–5.0.

The mixture was carefully skimmed from the top. Then the mixture was poured into units of wheat starch moulds and dried at room temperature to a moisture content of 5–10%.

Recipe I 210 g sugar (32%), 350 g dextrose (53%)

50 g water 100 g gelatine (15%) (solution no. 6)

The sugar mixture was boiled to 116° C. (boiling time 15 minutes). Then the mixture was cooled to 80° C. Gelatine was heated to 60° C. and stirred into the mixture. The mixture was left standing for 35 minutes at 35° C. The mixture had a final pH of 3.0–6.0.

The mixture was carefully skimmed from the top. Then the mixture was poured into units of wheat starch moulds and dried at room temperature to a moisture content of 5–10%.

Recipe J 210 g sugar (23%)

290 g dextrose (31%)

50 g water 350 g gum arabic (38%) (solution no. 2)

75 g gelatine (8%) (solution no. 6)

The sugar mixture was boiled to 120° C. (boiling time 25 minutes). Gum arabic was stirred into the mixture and the mixture was cooled to 90° C. Gelatine was heated to 60° C. and stirred into the mixture. The mixture was left standing for 80 minutes at 35° C. The mixture had a final pH of 3.0–5.5.

The mixture was carefully skimmed from the top. Then the mixture was poured into units of corn starch moulds and dried at room temperature to a moisture content of 5–10%.

Recipe K 210 g sugar (20%)

350 g dextrose (34%)

50 g water 400 g gum arabic (39%) (solution no. 2)

75 g gelatine (7%) (solution no. 7)

The sugar mixture was heated to 120° C. (boiling time 20 minutes). Gum arabic was added. Then the mixture was cooled to 100° C. Gelatine was heated to 70° C. and added to the mixture. The mixture was left standing 100 minutes at 35° C. The mixture had a final pH of 4.5–5.0.

The mixture was carefully skimmed from the top. Then the mixture was poured into units of wheat starch moulds and dried at room temperature to a moisture content of 5–10%.

Additional ingredients

The samples marked I are without any additives. Samples marked II has added citric acid (pH-value listed in the different recipes). Samples marked III–VII has added citric acid and flavouring as listed in the following:

I No additive

II Citric acid

III Essence of peppermint

IV Anis (powdered)

V Essence of almond

VI Cocoa

Tobacco powder

Solutions of gum arabic

Solution 9 (50% gum arabic)

2000 g of gum arabic was poured into 2000 g of warm water (50° C.). The solution was stirred vigorously and left standing for 24 hours with occasional vigorous stirring. Two exactly similar portions were mixed.

Solutions of gelatine

Solution 10 (33.3% gelatine)

100 g of gelatine was stirred into 100 g of warm water (70° C.) to produce a uniform mixture. Additionally 100 g of warm water (70° C.) was stirred into the mixture. Then the mixture was left standing for 5 hours.

Recipe M 400 g sugar (33%)

70 g water 100 g dextrose (8%)

100 g gelatine (8%) (solution no. 10)

600 g gum arabic (50%) (solution no. 9)

Water and sugar was stirred together under heating until the sugar was melted. Dextrose was added and heated to 120° C. (boiling time 15 minutes). Then gelatine was heated to 70° C. and stirred into the mixture. Gum arabic was stirred homogenously into the mixture. One half (M') of the mixture was decanted and stored at rest for 80 minutes at 35° C. The second half was boiled for an additional 35 minutes and then set to rest for 80 minutes at 35° C. The mixtures had a final pH of 3.5–5.0.

The mixtures M and M' were both carefully skimmed from the top. Then the mixture M' was poured into units of corn starch moulds and dried at 50° C. to a moisture content of 5–10%, and the mixture M was poured into units of wheat starch moulds and dried at 50° C. to a moisture content of 5–10%.

Recipe O 400 g sugar (29%)

70 g water 100 g dextrose (7%)

900 g gum arabic (64%) (solution no. 9)

The sugar and water were stirred together under heating until sugar was melted. Dextrose was added and heated to 117° C. (boiling time 13 minutes). Gum arabic was added and stirred until a homogenous mixture. One half (O') was decanted and set to rest for 65 minutes at 35° C. The second half was boiled for additional 45 minutes and then set to rest for 70 minutes at 35° C. The mixtures had a final pH of 3.0–5.0.

The mixtures O and O' were both carefully skimmed from the top. Then both the mixture were poured into units of corn starch moulds and dried at 50° C. to a moisture content of 5–10%.

Recipe P 400 g sugar (27%)

70 g water 100 g dextrose (7%)

10000 g gum arabic (67%) (solution no. 9)

The sugar and water were stirred together under heating until sugar was melted. Dextrose was added and heated to 118° C. (boiling time 12 minutes). Gum arabic was added and stirred until a homogenous mixture. One half (P') was decanted and set to rest for 70 minutes at 35° C. The second half boiled for an additional 50 minutes and then set to rest for 120 minutes at 35° C. The mixtures had a final pH of 4.0–5.0.

The mixtures P and P' were both carefully skimmed from the top. Then the mixture P' was poured into units of corn starch moulds and dried at 50° C. to a moisture content of 5–10%, and the mixture P was poured into units of wheat starch moulds and dried at 50° C. to a moisture content of 5–10%.

Additional ingredients used in recipes M–P

Samples marked I were prepared without addition of any additional ingredients. Samples marked II were prepared with addition of nicotine after initial pregelling (pH unchanged). Samples marked III were prepared with addition of as well nicotine as citric acid.

In the following examples recipe Q and recipe R form the basis of various stimulant units to which have been added specific quantities of the active ingredient as well as of tobacco flavouring. These stimulant units are based on gum arabic solution no. 11.

Solution 11 (50% gum arabic)

1500 g of gum arabic was stirred into 1500 g of warm water (50° C.). Then the mixture was left standing for approx. 40 hours.

Recipe Q 200 g sugar (25.6%)
30 g water
80 g dextrose (10.3%)
500 g gum arabic (64.1%) (solution no. 11)
Ingredients added:
I 4 ml 10% nicotine base
II 1 ml 50% tobacco flavouring ~1 g
III 5 g $Na_2CO_3$+5 g $NaHCO_3$ Water and sugar was stirred together under heating until the sugar was melted. Dextrose was added and heated to 116° C. (boiling time 14 minutes). Gum arabic was stirred into the mixture until a homogenous mixture. The mixture was slowly boiled for 26 minutes—until it was limpidity. Then the mixture was left standing to rest for 155 minutes at approx. 30° C., and subsequently the mixture was skimmed off.

$Q^1$ and $Q^2$
I and II added.
Nicotine content: 0.5–1.0 mg/g
Content of tobacco flavouring: 1.0–1.5 mg/g
pH: approx. 5.0
$Q^3$
Similar to $Q^1$ and $Q^2$+III.
Nicotine content: 0.5–1.0 mg/g
Content of tobacco flavouring: 1.0–1.5 mg/g
$Na_2CO_3$: approx. 1.3%
$NaHCO_3$: approx. 1.3%
pH: approx. 9.0

Recipe R 200 g sugar (25.8%)
30 g water
76 g dextrose (9.8%)
500 g gum arabic (64.4%) (Solution no. 11)
Ingredients added:
I: 4 ml 10% nicotine base
II: 1 ml 50% tobacco flavouring ~1 g
IV: 7.5 g $NaCO_3$ dissolved in 15 ml water
V: 7.5 g $NaHCO_3$ dissolved in 15 ml water
VI: 5.0 g $NaCO_3$ dissolved in 5 ml water
VII: 5.0 g $NaHCO_3$ dissolved in 5 ml water The mixture was boiled in the same manner as described in recipe Q using the following parameters:
Boiling temperature 120° C.
Boiling time 12 minutes
Slow boiling time 28 minutes
Resting time 150 minutes
$R^1$ and $R^2$
I+II+IV+V added.
Nicotine content: 0.5–1.0 mg/g
Content of tobacco flavouring: 1.0–1.5 mg/g
$Na_2CO_3$ content: approx. 0.9%
$NaHCO_3$ content: approx. 0.9%
pH: approx. 8.0
$R^3$
Equivalent to $R^1$+$R^2$+VI+VII.
Nicotine content: 0.5–1.0 mg/g
Content of tobacco flavouring: 1.0–1.5 mg/g
$Na_2CO_3$ content: approx. 2.3%
$NaHCO_3$ content: approx. 2.3%
pH: approx. 9.0
$R^3$+$Q^3$ mixture
Nicotine content: 0.5–1.0 mg/g
Content of tobacco flavouring: 1.0–1.5 mg/g
$Na_2CO_3$ content: approx. 1.8%
$NaHCO_3$ content: approx. 1.8%
pH: approx. 9.0

All samples marked Q and R were dried in starch moulds at 50° C.

Note: Those contents which are listed in the total mixtures are in all cases reported as contents of dry matter. Also after incorporation of the carbonate buffer and before drying in the starch moulds, the solutions should not be reheated in order to prevent production of $CO_2$.

Measuring of texture profiles

Texture profile analysis according to the above-mentioned method of Sanderson et al., ibid, was performed according to the following procedure:

(a) Procedure

A cylindrical sample of 15 mm in diameter and 7–10 mm in height is prepared and placed between two compression blades of a Materials Testing Machine, J. J. Instrument M 30 K, Lloyd Instruments, PLC. The plates are surrounded by a heating element to ensure a selected constant temperature.

The sample is compressed twice at a rate of compression of 50 mm/minute to 70% of its original height while the force provided by the material is concurrently measured and recorded.

After the first compression, the compression plates are withdrawn to their original position and the second compression cycle is immediately initiated.

(b) Sample preparation

Samples for texture analysis are prepared by placing one or more stimulant units in a compression mould having an inner diamter of 15 mm and a compression piston. Then the mould and its content is placed in an oven for 10–15 minutes at 80° C. After removal a pressure of about 3 kg is applied to the compression piston until the sample obtains form stability at room temperature. The mould and its content is then cooled by means of liquid $N_2$, whereafter the texture sample is expelled from the mould.

(c) Sample conditioning

The samples for texture analysis are placed in a water-tight polyethylene bag at the desired temperature, e.g. room temperature of 35° C., for 24 hours.

Measuring of disintegration times

Further, in a number of cases disintegration times according to Ph. Eur. 2. Ed., V. 5.1.1., were measured according to the following procedure:

(a) Procedure

Test samples having dimensions of 10 mm×10 mm×5 mm, and weights of 0.5–1.5 g, are placed in cylindrical glass tubes, which are supported by a rigid assembly and suspended in a breaker containing purified water at 37° C. of a disintegration test apparatus, type: Pharma Test PT21.

The disintegration time is measured as the time it takes for the last sample unit to disappear.

(b) pH measurement pH is measured by means of a pH-meter, type: Metrohm 691.

Results

The results are shown in Tables 1 and 2.

TABLE 1

| Texture Parameter | Preparation | | | | | |
|---|---|---|---|---|---|---|
| | BII | CIII | FI | MII | MIII | OI |
| Firmness (N/cm²) | 690 | 170 | 1960 | 450 | 310 | 1280 |
| Hardness (N/cm²) | 100 | 20 | 270 | 80 | 60 | 210 |
| Brittleness (%) | >30% | >30% | >30% | >30% | >30% | >30% |
| Adhesiveness (%) | ~0 | ~0 | ~0 | ~0 | ~0 | ~0 |
| Elasticity (%) | 88 | 83 | 88 | 86 | 87 | 91 |
| Cohesiveness (%) | 50 | 44 | 54 | 68 | 70 | 61 |

Note: Texture parameters were measured at 35° C.

TABLE 2

| Disintegration | Preparation | | | | |
|---|---|---|---|---|---|
| Disintegration | BI | CI | FII | OII | OIII |
| time (min) | 31,6 | 32,0 | 28,0 | 33,6 | 38,5 |

Note: Disintegration times were measured at 37° C.

The stimulant units prepared according to the rest of the preparations A–R showed textural parameters and disintegration times within the defined ranges of claim 1.

The buffering ability of stimulant units according to the invention is illustrated by the measurement of pH for a 1.0773 g test sample unit of recipe R which disintegrated with a disingration time of 25.26 minutes. The following pH values were obtained:

| Time (minutes) | pH |
|---|---|
| 5 | 8.66 |
| 10 | 8.84 |
| 15 | 8.95 |
| 20 | 9.01 |
| 25 | 8.89 |

What is claimed is:

1. A saliva-soluble stimulant unit comprising an active ingredient in a gel, wherein the gel is prepared by gelling a water-binding gelling agent, and the active ingredient comprises nicotine or alkaloid having the same direction of activity, said unit having
   i) a texture profile, determined by texture profile analysis, with parameter values within the following ranges:
      a) firmness provided by a modulus greater than 100 N/cm²;
      b) hardness provided by a maximum force occurring during a first compression cycle of greater than 5 N/cm²;
      c) brittleness provided by a strain percentage required to break the gel of at least 30%;
      d) adhesiveness provided by a ratio between the area of the negative peak between two compression cycles and the area of the first peak of from 0% to 70%;
      e) elasticity provided by a ratio 100×(D−d)/D within the range from 25% to 100%, where D is the sample height (cm) before a first compression cycle, and d is the permanent deformation of the sample (cm) before a second compression cycle; and
      f) cohesiveness provided by a total work ratio between first and second compression cycles within the range from 25% to 100%;
   ii) a disintegration time, measured at 37° C. using a disintegration test apparatus according to Ph. Eur. second edition, within the range 5–60 minutes;
   iii) a nicotine content from 0.5 to 10 mg or a corresponding content of alkaloid; and
   (iv) a physiologically acceptable buffering substance or agent.

2. A stimulant unit according to claim 1, wherein the texture profile has parameter values within the following ranges:
   a) firmness greater than 200 N/cm²;
   b) hardness greater than 25 N/cm²;
   c) brittleness of at least 30%;
   d) adhesiveness from 0% to 40%;
   e) elasticity within the range from 50% to 100%; and
   f) cohesiveness within the range from 40% to 100%; and the disintegration time is within the range 6–45 minutes.

3. A stimulant unit according to claim 1, wherein the texture profile has parameter values within the following ranges:
   a) firmness greater than 400 N/cm²;
   b) hardness from 80 to 300 N/cm²;
   c) brittleness of at least 30%;
   d) adhesiveness from 0% to 20%;
   e) elasticity within the range from 80% to 100%; and
   f) cohesiveness within the range from 40% to 100%; and the disintegration time is within the range 15–40 minutes.

4. A stimulant unit according to claim 1, wherein the gelling agent comprises gelatine or one or more synthetic or natural polysaccharides.

5. A stimulant unit according to claim 1, wherein the gelling agent comprises a confectionary polysaccharide.

6. A stimulant unit according to claim 1, wherein the gelling agent is selected from the group consisting of agar, algin, carrageenan, guar gum, gum arabic, gum ghatti, gum tragacanth, karaya gum, locust bean gum, pectin, and xanthan gum.

7. A stimulant unit according to claim 1, wherein the gelling agent is gum arabic.

8. A stimulant unit according to claim 1, further comprising flavour and aroma additives.

9. A stimulant unit according to claim 8, wherein the flavour and aroma additives comprise one or more synthetic or natural flavour agents selected from the group consisting of essential oils, essences, fruit juices, powders, flours, and mint.

10. A stimulant unit according to claim 9, wherein the comminuted vegetable material is selected from the group consisting of comminuted tobacco, comminuted coffee, and comminuted tea.

11. A stimulant unit according to claim 1, further comprising a vitamin or mineral additive.

12. A stimulant unit according to claim 1, wherein a sufficient amount of the buffering substance or agent is provided to ensure a saliva pH of 8–10 during disintegration of the unit.

13. A stimulant unit according to claim 12, wherein the amount of buffering substance or agent in a unit is from 5 mg to 50 mg.

14. A stimulant unit according to claim 12, wherein the buffering substance or agent is selected from the group consisting of alkali metal carbonates, bicarbonates, phosphates, hydrogen phosphates, and mixtures thereof.

15. A stimulant unit according to claim 1, comprising from 0.5 to 5.0 mg of nicotine.

16. A stimulant unit according to claim 1, comprising from 1.0 to 1.5 mg of nicotine.

17. A stimulant unit according to claim 1, comprising from 1.5 to 2.5 mg of nicotine.

18. A stimulant unit according to claim 1, comprising from 2.5 to 3.0 mg. of nicotine.

19. A stimulant unit according to claim 1, wherein the nicotine is homogeneously distributed throughout the unit to provide a substantially constant release of nicotine.

20. A stimulant unit according to claim 1, wherein the nicotine is inhomogeneously distributed in a multi-layered unit to provide a graduated release comprising a priming and a sustained release.

21. A stimulant unit according to claim 1, wherein the unit is provided in a shape suitable for adherence to the palate.

22. A saliva-soluble stimulant according to claim 1, wherein said saliva-soluble stimulant unit is produced by extrusion.

23. A salive-soluble stimulant unit according to claim 22, wherein said saliva-soluble stimulant unit produced by extrusion is further cut to form tablets.

24. A saliva-soluble stimulant unit according to claim 1, wherein said saliva-soluble stimulant unit is prepared by casting.

25. A salive-soluble stimulant unit according to claim 24, wherein said salive-soluble stimulant unit is prepared by casting in cavities produced in a starch material.

* * * * *

UNITED STATES PATENT AND TRADEMARK OFFICE
CERTIFICATE OF CORRECTION

PATENT NO. : 5,733,574

DATED : MARCH 31, 1998

INVENTOR(S) : DAM

It is certified that error appears in the above-identified patent and that said Letters Patent is hereby corrected as shown below:

On the cover page, in [63] Related U.S. Application Data, please change "170,455" to —170,445—.

In column 1, line 3, change "170,455" to —170,445—.

In column 1, line 48, change "discontinous" to —discontinuous—.

In column 1, line 54, change "widen" to —with—.

In column 3, line 37, change "salive" to —saliva—.

In column 5, line 45, change "Continous" to —Continuous—.

In column 5, line 46, change "continous" to —continuous—.

In column 5, line 64, change "blod" to —blood—.

In column 7, line 20, change "nor-nicotine" to —non-nicotine—.

In column 7, line 59, change "dextroxe" to —dextrose—.

In column 8, line 3, change "ressins" to —resins—.

In column 8, line 18, change "rom" to —rum—.

In column 9, line 8, change "vitamine" to —vitamin—.

UNITED STATES PATENT AND TRADEMARK OFFICE
CERTIFICATE OF CORRECTION

PATENT NO. : 5,733,574

DATED : MARCH 31, 1998

INVENTOR(S) : DAM

It is certified that error appears in the above-identified patent and that said Letters Patent is hereby corrected as shown below:

column 9, line 23, change "phasphate" to —phosphate—.

column 9, line 44, change "gellies" to —jellies—.

column 10, line 45, change "shold" to —should—.

column 11, line 29, change "jaketed" to —jacketed—.

column 11, line 45, change "continous" to —continuous—.

column 11, line 59, change "eater" to —water—.

column 12, line 62, change "(23°F)" to —(230°F)—.

column 16, line 62, change "on to" to —onto—.

column 19, line 20, change "gellies" to —jellies—.

column 19, line 21, change "gellies" to —jellies—.

UNITED STATES PATENT AND TRADEMARK OFFICE
CERTIFICATE OF CORRECTION

PATENT NO. : 5,733,574
DATED : March 31, 1998
INVENTOR(S) : DAM

It is certified that error appears in the above-identified patent and that said Letters Patent is hereby corrected as shown below:

column 30, line 8, in claim 23, change "salive" to ---saliva---.

column 30, line 14, in claim 25, change "salive" to ---saliva---.

column 30, line 15, in claim 25, change "salive" to ---saliva---.

Signed and Sealed this

Eleventh Day of May, 1999

*Attest:*

Q. TODD DICKINSON

*Attesting Officer*     Acting Commissioner of Patents and Trademarks